(12) United States Patent
Miller (10) Patent No.: US 12,059,130 B2
(45) Date of Patent: Aug. 13, 2024

(54) DEVICE DELIVERY SYSTEMS FOR ENDOSCOPES

(71) Applicant: GI Scientific, LLC, Arlington, VA (US)

(72) Inventor: Scott Miller, Arlington, VA (US)

(73) Assignee: GI Scientific, LLC, Arlington, VA (US)

( * ) Notice: Subject to any disclaimer, the term of this patent is extended or adjusted under 35 U.S.C. 154(b) by 1071 days.

(21) Appl. No.: 16/955,004

(22) PCT Filed: Jan. 6, 2019

(86) PCT No.: PCT/US2019/012448
§ 371 (c)(1),
(2) Date: Jun. 17, 2020

(87) PCT Pub. No.: WO2019/136326
PCT Pub. Date: Jul. 11, 2019

(65) Prior Publication Data
US 2020/0390319 A1    Dec. 17, 2020

Related U.S. Application Data

(60) Provisional application No. 62/614,999, filed on Jan. 8, 2018.

(51) Int. Cl.
*A61B 1/00* (2006.01)
*A61B 1/012* (2006.01)
(Continued)

(52) U.S. Cl.
CPC ...... *A61B 1/00137* (2013.01); *A61B 1/00096* (2013.01); *A61B 1/00112* (2013.01);
(Continued)

(58) Field of Classification Search
USPC ....................................................... 600/124
See application file for complete search history.

(56) References Cited

U.S. PATENT DOCUMENTS 5,707,344 A * 1/1998 Nakazawa ......... A61B 1/00066
600/125
5,944,657 A * 8/1999 Djurovic ............ A61B 17/0218
600/218

(Continued)

FOREIGN PATENT DOCUMENTS

| DE | 3532609 A | 3/1987 |
| JP | 200217655 A | 1/2002 |
| JP | 2010063721 A | 3/2010 |

OTHER PUBLICATIONS

Machine language translation of DE 35 32 609 to Dagn, Mar. 1987 (Year: 1987).*

(Continued)

*Primary Examiner* — John P Leubecker
(74) *Attorney, Agent, or Firm* — Farber LLC (57) ABSTRACT

Tools and systems are provided for the delivery of accessory devices to endoscopes. A device delivery system for delivering an endoscopic device to an endoscope, comprises an insertion instrument having a pair of pivotable arms. The arms extend from a device delivery portion of the insertion instrument at a first end, into a handle portion at an opposed, second end, and are connected together at a pivotable connection. A bracket is connected to a back plate for placement of a device to be delivered thereagainst. An extension shaft extends from the back plate for placement through a working channel of the endoscopic device to be delivered. The system further comprises a removable spacer for enclosing the device delivery end of the insertion instrument.

10 Claims, 11 Drawing Sheets

(51) Int. Cl.
*A61B 17/00* (2006.01)
*A61B 90/00* (2016.01)

(52) U.S. Cl.
CPC ........ *A61B 1/00149* (2013.01); *A61B 1/0125* (2013.01); *A61B 17/00234* (2013.01); *A61B 2017/00296* (2013.01); *A61B 2017/0034* (2013.01); *A61B 2017/0046* (2013.01); *A61B 2017/00477* (2013.01); *A61B 2090/0807* (2016.02)

(56) References Cited

U.S. PATENT DOCUMENTS

| | | | | |
|---|---|---|---|---|
| 6,049,960 | A * | 4/2000 | Pilling | B25B 27/28 29/450 |
| 6,792,837 | B2 | 9/2004 | Battistone | |
| 7,648,457 | B2 * | 1/2010 | Stefanchik | A61B 1/012 606/1 |
| 8,469,878 | B2 * | 6/2013 | Ushijima | A61B 1/00101 600/101 |
| 8,920,311 | B2 * | 12/2014 | LaBombard | A61B 1/00101 600/125 |
| 9,516,994 | B2 * | 12/2016 | Sato | A61B 8/4494 |
| 11,510,554 | B1 * | 11/2022 | Aurilia | A61B 1/0011 |
| 2001/0018596 | A1 * | 8/2001 | Selmon | A61M 29/02 606/198 |
| 2003/0032975 | A1 * | 2/2003 | Bonutti | A61B 17/0218 606/192 |
| 2005/0125005 | A1 * | 6/2005 | Fujikura | A61B 1/00101 606/116 |
| 2006/0270978 | A1 | 11/2006 | Binmoeller | |
| 2007/0149850 | A1 * | 6/2007 | Spivey | A61B 1/00142 600/127 |
| 2007/0270897 | A1 | 11/2007 | Skerven | |
| 2010/0017414 | A1 | 1/2010 | Leeds et al. | |
| 2010/0305404 | A1 * | 12/2010 | Ushijima | A61B 1/00101 600/127 |
| 2011/0105840 | A1 * | 5/2011 | Terliuc | A61B 1/00131 600/104 |
| 2011/0241460 | A1 | 10/2011 | Jiang | |
| 2014/0027578 | A1 | 1/2014 | Comtesse | |
| 2015/0065795 | A1 | 3/2015 | Titus | |
| 2016/0022120 | A1 * | 1/2016 | Terliuc | A61B 1/00082 600/124 |
| 2016/0051135 | A1 | 2/2016 | Greenberg et al. | |
| 2017/0066111 | A1 | 3/2017 | Wang | |
| 2017/0251910 | A1 | 9/2017 | Surti et al. | |
| 2017/0311789 | A1 | 11/2017 | Mulcahey et al. | |
| 2017/0311974 | A1 | 11/2017 | Friedrichs | |
| 2018/0160886 | A1 | 6/2018 | Govani et al. | |
| 2018/0206708 | A1 | 7/2018 | Miller | |
| 2019/0009963 | A1 | 1/2019 | Wessely | |
| 2019/0070998 | A1 | 3/2019 | Spencer et al. | |
| 2019/0142242 | A1 * | 5/2019 | Yamaya | A61B 1/0011 600/101 |
| 2020/0107703 | A1 * | 4/2020 | Quinn | A61B 1/00142 |

OTHER PUBLICATIONS

International Search Report and Written Opinion dated Dec. 16, 2020 for PCT Appl. No. PCT/US2020/65429.
International Search Report and Written Opinion dated Dec. 16, 2020 for PCT Appl. No. PCT/US2020/65424.
International Search Report and Written Opinion dated Dec. 16, 2020 for PCT Appl. No. PCT/US2020/65427.
United States Patent and Trademark Office; International Search Report and Written Opinion; PCT/US2019/012448; Apr. 16, 2019.

* cited by examiner

DEVICE DELIVERY SYSTEMS FOR ENDOSCOPES

CROSS-REFERENCE TO RELATED APPLICATIONS

This application claims benefit of U.S. Provisional Application No. 62/614,999, filed Jan. 8, 2018, the entire contents of which are incorporated herein by reference.

TECHNICAL FIELD

The present disclosure relates to tools and systems for the delivery of medical devices or components, and specifically, to tools and systems that assist or facilitate the delivery of one or more medical devices or components over, onto, into, or against, another medical device or component. More specifically, the present disclosure provides delivery tools and systems for the placement of an endoscopic device over, onto, into, or against, another instrument or endoscope.

BACKGROUND

Recent advances in optical imaging technology have allowed many medical procedures to be performed today in a minimally invasive manner. The evolution of the more sophisticated, flexible scope with advanced visual capabilities has allowed access to regions deep within the human body that could only be achieved before with invasive surgical intervention. This modern day convenience has resulted in an increase in the demand for, as well as the number of, endoscopic, laparoscopic, arthroscopic, ophthalmoscopic, borescopic, or other remote imaging visualization procedures performed every year in the U.S.

Endoscopy, for instance, is a procedure in which a lighted visualization device called an endoscope is inserted into the patient's body to look inside a body cavity or organ for the purpose of examination, diagnosis or treatment. The endoscope may be inserted through a small incision or through a natural opening of the patient. In a bronchoscopy, the endoscope is inserted through the mouth, while in a sigmoidoscopy, the endoscope is inserted through the rectum. Unlike most other medical imaging devices, endoscopes are inserted directly into the organ.

Most endoscopes are used in combination with other medical devices or accessories that are now available for additional benefits. For instance, devices that serve as convenient accessories for currently existing endoscopes to reduce the risk of contamination and infection that occur with reuse of the scope, while also improving the performance of the endoscope, have recently been developed. In some cases, the accessory can be configured for a duodenoscope, and allows the user to simultaneously protect the working end from bacterial contamination as well as enables instruments to exit out of the working end of the scope at different angles with ease. Other endoscope accessories include, for example, distal caps, variceal banding devices, and scope sheaths. All of these scope accessories are designed to fit onto an endoscope and rely on a precise fit of the accessory on the distal or working end of the endoscope. If the accessory or component is compromised, the performance of the accessory and the endoscope itself is adversely affected.

Accordingly, there is a need to improve the attachment process of these scope accessories onto existing scopes. As is the case whenever one medical device or accessory is intended to be fitted over, onto, into, or against, another medical device or accessory where there is very limited range of space or clearance between the two components, the fitting and delivery process can be a challenge. This is especially the case when the different components have different diameters, lengths, surface finishes, coefficients of friction, shapes, geometries, tapers, dimensions, and other material properties or characteristics or features, yet must work in a compatible manner for effective delivery and matching of the one or more components to another component. There is thus a real desire to fit the medical components together properly, without causing damage to either of these medical components (most of which are highly sensitive and delicate to physical disturbance), in an expeditious manner so as to avoid improper fittings, overhandling and loss of time during procedures.

BRIEF SUMMARY

The present disclosure provides device delivery assistance for the proper fitting of medical devices or components together in an expeditious manner. Specifically, the present disclosure provides tools and systems that assist or facilitate the delivery of one or more medical devices or components over, onto, into, or against, another medical device or component.

According to one aspect of the invention, one of the medical devices or components is an endoscope accessory such as, for example, a distal cap, variceal banding device, scope sheath, scope seal, or other accessory for coupling to the scope, while the other medical device is a scope such as, for example, an endoscope or duodenoscope.

In some embodiments, the delivery system may comprise a delivery assistance tool and an introducer tool. The delivery assistance tool may be configured for attachment to the proximal end of the scope accessory, while the introducer tool may be configured for attachment to the distal end of the scope accessory. The delivery assistance tool serves to expand the proximal end or opening of the scope accessory, thus enabling an easier insertion process with respect to the scope. The insertion tool allows the steady handling and proper alignment of the scope accessory with respect to the scope. The combination of the delivery assistance tool and the insertion tool may provide an accurate, fast and convenient attachment process of the scope accessory to the scope in one smooth motion, including by virtue of the delivery system, expanding the scope accessory temporarily as it is delivered on to a scope and then allowing the scope accessory to contract to a different dimension as the delivery system or a portion thereof is removed.

The insertion tool may include a gripping portion for the user to hold the tool, while the main body of the tool may be configured to grasp and securely cradle the scope accessory. In some embodiments, the main body of the insertion tool may further include a pair of stabilizing arms, which may extend into pads that can cooperate with flanged pads on the sides of the delivery assistance tool. The user may grip both pads during use to better stabilize and more accurately position the scope accessory in the delivery process.

The delivery assistance tool may be inserted into the opening of the scope accessory at the proximal end, and include squeeze paddles, enabling a quick expansion of the scope accessory opening for placement over the scope. In a resting position, however, the delivery assistance tool does not stretch out or expand the scope accessory. The delivery assistance tool may be formed by wireform and overmolded with respect to the scope accessory, or may be a separate plastic part that is inserted and packaged together with the scope accessory. A tab may be provided with the tool for ease of handling. The tool may be formed of an elastomeric material to facilitate expansion. It is contemplated that the tool may be pulled away or pulled free as the accessory is inserted onto the scope by breaking the tool away. That may be accomplished by providing a weakened, scored section for a breakaway portion, or it may be accomplished with a weaker material at that area to be broken free.

In some embodiments, the delivery assistance tool may be provided with a flared insertion collar having a trumpet-like shape that may be broken off the scope after the scope accessory is in place. This insertion collar may be formed of rigid or semi-rigid material to hold the opening of the scope accessory during insertion, stabilizing it from wrinkling or bunching. In addition to its flared shape, the collar 48 may include a cutaway portion, such as a V cut to give the user a view through the insertion collar as the user aims a working channel extension shaft of the insertion tool through the accessory. The ramped shape of the insertion collar guides the device or accessory into and over the scope during use. Furthermore, the fluted shape of the collar creates a flange ring grip to easily pull and separate the insertion collar 48 from the accessory once the delivery process is completed.

The flared portion of the insertion collar may be attached to the main shaft that is inserted into the accessory by a glue bond that allows the flared portion to tear away from the accessory once delivery is complete. In an alternative embodiment, the insertion collar may include a tear away portion such as a scored or hatch marked area that allows quick breaking away of the flared ring from the scope accessory. The main shaft of the delivery assistance tool may include surface features such as hard inner ribs that support and stabilize the scope accessory during this delivery process.

In some embodiments, the scope accessory may be attached to the delivery tool in a resting state (i.e., unexpanded). In some embodiments, a hard plastic co-molded component may be provided that cooperates with the elastomeric portion of the scope accessory such that, upon squeezing the nose of the scope accessory, the molded structure which may be part of the optical window component opens up, thereby also expanding the elastomer of the scope accessory allowing it to more easily fit onto the scope. Releasing the force on the nose puts the scope accessory back in a resting state.

In some embodiments, hard plastic prongs may be provided as part of the scope accessory. For instance, the scope accessory may be provided with its elastomeric skirt rolled back over itself to expose the prongs, which serve to help splint the elastomeric skirt and keep it from bunching, while also providing a glide surface to facilitate insertion over the scope. When the elastomeric skirt is rolled back over, the scope accessory is properly sealed against the scope.

In accordance with another aspect of the present disclosure, the elastomeric skirt of the scope accessory may be further secured onto the scope after delivery by the application of heat. The application of low heat to an elastomeric skirt formed of a heat-shrinking material, such as for example, fluorinated ethylene propylene (FEP), polytetrafluoroethylene (PTFE), polyester (PET), polyvinyl chloride (PVC), polyolefin, or any other suitable polymeric material, can cause the skirt portion of the scope accessory to shrink around the scope, forming a tight seal.

In still another exemplary embodiment, a delivery system is provided. This delivery system may comprise an insertion instrument and an associated end cap or spacer. The delivery system may be provided with a pre-mounted scope accessory and provide an integrated tool for delivery. The insertion instrument may have a handle portion or end, and a working or delivery end. The insertion instrument may generally have the structure and functionality of delivery pliers, and include a first or upper arm and a second or lower arm. These arms may be connected to one another at a hinged or pivotal connection through secondary arm extensions, respectively. The insertion instrument may further include a main bracket and a back plate or wall connected to this main bracket for placement of the scope accessory against thereof. The bracket is stationary relative to the arms. The back plate may be connected to a stabilizing extension shaft, which may be inserted through a working channel opening of the scope accessory, and also serve as an alignment guide during the assembly process.

Each of the upper and lower arms may also include stabilizing or side bars. The stabilizing side bars may each have a ratcheting surface or feature comprising teeth, ridges, or other surface protrusions, that allows the stabilizing side bars to lock together and prevent movement of the arms relative to one another.

An end cap or spacer is provided for use with the insertion instrument. This spacer comprises a two-piece design and includes removable spacer components. The spacer can be placed at the working end of the insertion instrument to enclose the attached scope accessory. The spacer may be configured so that it expands the opening of the scope accessory for placement over the distal end of the scope. Collectively, these spacer elements 340a, 340b form an additional delivery assistance tool for delivering the scope accessory at the working or delivery end of the insertion instrument to the scope. Indicia may also be provided on the delivery system to guide proper positioning of the scope accessory relative to the scope on which it is being placed.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

DESCRIPTION OF THE EMBODIMENTS

In order to illustrate the principles of the invention, the present embodiments are shown and described with respect to a scope accessory such as, for example, a distal cap, variceal banding device, scope sheath, scope seal or cap, or other scope accessory, and a scope such as, for example, an endoscope or duodenoscope. It is contemplated that the scope could comprise a side-viewing or end-viewing scope.

Figure 1:
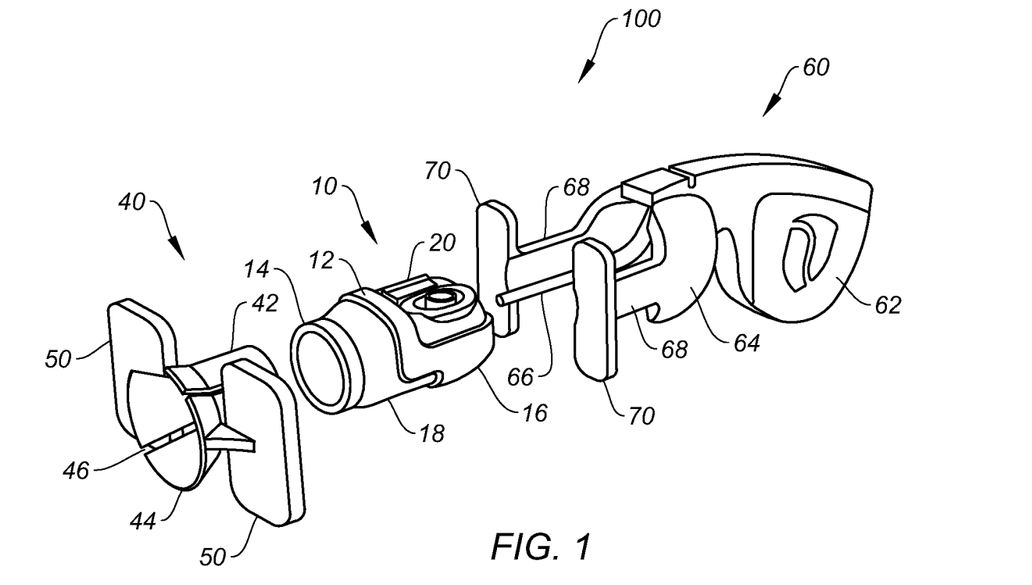
FIG. 1 illustrates an exploded view of a delivery system in use with a scope accessory, in accordance with an exemplary embodiment of the present disclosure.
Figure 2:
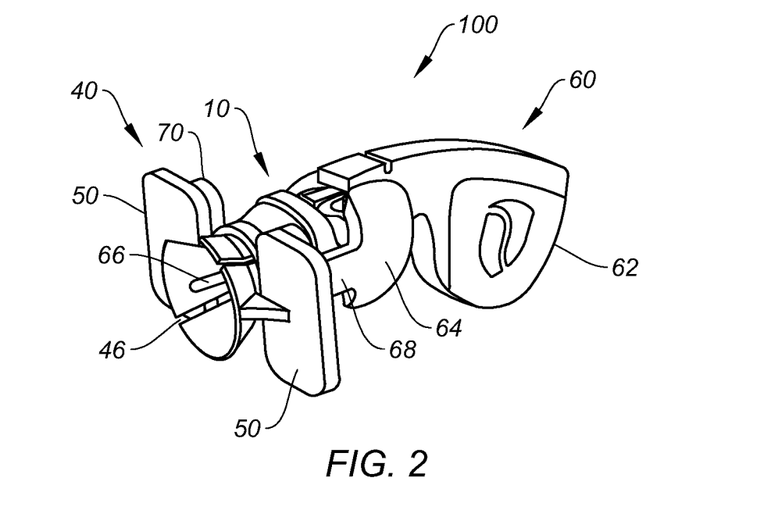
FIG. 2 shows the delivery system of FIG. 1 coupled with the scope accessory.

Turning now to the drawings, FIGS. 1 and 2 illustrate an exemplary embodiment of a device delivery system 100 of the present disclosure that can be used with a scope accessory 10 of the type for use with an endoscope. The scope accessory 10 can be of the type that couples to the endoscope working end, and seals and covers infection prone areas of the scope to prevent ingress of debris, fluid, or other unwanted matter that could lead to bacterial contamination and decreased performance of the scope. In addition, the scope accessory 10 can provide a flexible working channel for instruments to be inserted into the scope. The flexible working channel can be angularly adjustable with ease. By way of example, a suitable scope accessory that can be used with the delivery systems and tools of the present disclosure is described in U.S. Patent Application Publication No. 2018/0206708 A1, the contents of which are herein disclosed by reference.

As FIG. 1 illustrates, the scope accessory 10 may comprise a main body 12, proximal end 14 and distal end 16, lower surface 18 and upper surface 20. The proximal end 14 attaches onto a working or distal end of a scope, extending the working end portion of the scope. The delivery system 100 may comprise a delivery assistance tool 40 and an insertion tool 60. The delivery assistance tool 40 may be configured for attachment to the proximal end 14 of the scope accessory 10, while the insertion tool 60 may be configured for attachment to the distal end 16 of the scope accessory 10, as illustrated in FIG. 2. The delivery assistance tool 40 serves to expand the proximal end 14 or opening of the scope accessory 10, thus enabling an easier insertion process with respect to the scope. The insertion tool 60 allows the steady handling and proper alignment of the scope accessory 10 with respect to the scope. The combination of the delivery assistance tool 40 and the insertion tool 60 may provide an accurate, fast and convenient attachment process of the scope accessory 10 to the scope in one smooth motion.

The delivery assistance tool 40 may include a tubular main body 42 for insertion into the receiving end or proximal end 14 of the scope accessory 10. The main body 42 may include slits 46 or cutouts, slots or other designs that allow the tubular main body 42 to expand and contract in diameter. The tubular main body 42 extends to a flared collar 44, which may also include the slits 46, as shown in FIGS. 1 and 2. This flared collar 44 also includes flared brace pads 50 to assist with the manipulation of the delivery assistance tool 40.

The insertion tool 60 may include a gripping portion 62 for the user to hold the tool 60, while the main body 64 of the tool 60 may be configured to grasp and securely cradle the scope accessory 10, as shown in FIG. 2. In some embodiments, the main body 64 may have a tulip-shaped internal receiving cavity for cradling the scope accessory 10. In some embodiments, the main body 64 of the insertion tool 60 may further include a working channel extension shaft 66 and a pair of stabilizing arms 68, which may include flanged brace pads 70 that can cooperate with flanged brace pads 50 provided on the sides of the delivery assistance tool 40. This working channel extension shaft 66 may be inserted through a working channel opening of the scope accessory 10. The user may grip both pads 50, 70 during use to better stabilize and more accurately position the scope accessory 10 in the delivery process. Collectively, the delivery assistance tool 40 and the insertion tool 60 expands the receiving end of the scope accessory 10 while maintaining secure control over the scope accessory 10 as it is inserted over and onto the scope.

It is contemplated that either of the delivery assistance tool 40 or insertion tool 60 may be pulled away or pulled free as the accessory 10 is inserted onto the scope by breaking the tools 40, 60 away. That may be accomplished by providing a weakened, scored section for a breakaway portion, or it may be accomplished with a weaker material at that area to be broken free. Additional details, including optional features, of the delivery assistance tool 40 and the insertion tool 60, will be described below.

Figure 3A:
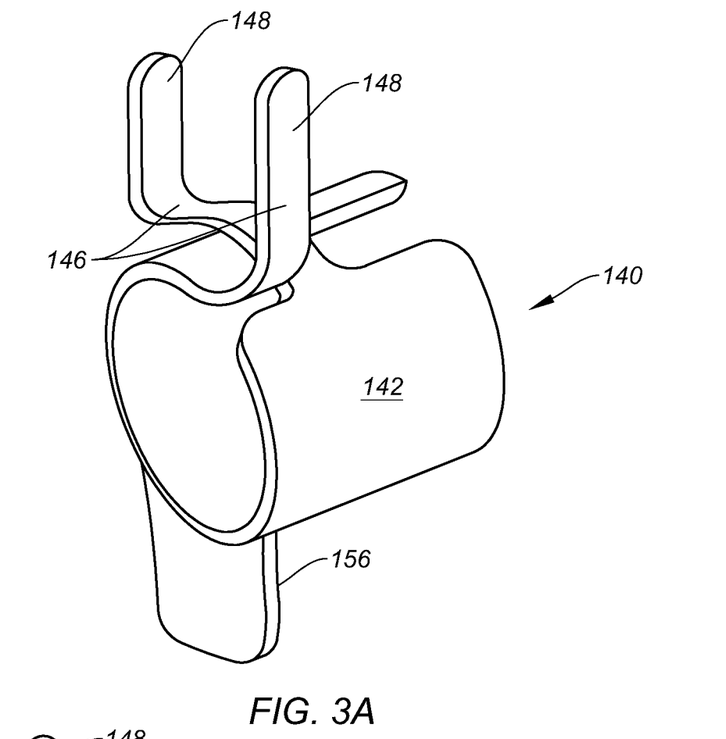
FIG. 3A shows a perspective view of a delivery assistance tool, in accordance with another exemplary embodiment of the present disclosure.
Figure 3B:
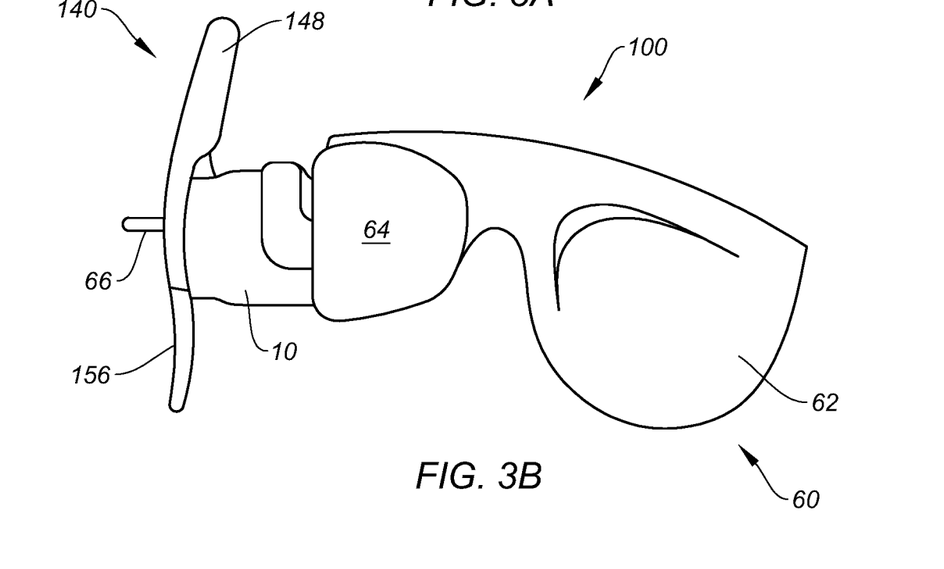
FIG. 3B illustrates a side view of the system and delivery assistance tool of FIG. 3A in use with a scope accessory.

FIGS. 3A and 3B illustrate another exemplary embodiment of a delivery assistance tool 140 of the present disclosure. The delivery assistance tool 140 includes a tubular main body 142 which may be inserted into the receiving end or opening of the scope accessory 10 at the proximal end 14. The tubular main body 142 may be formed as a sheet of material having extended tabs 146 which, when rolled into a cylinder, allows the extended tabs 146 to cross one another, as shown in FIG. 3A. The extended tabs 146 may terminate into angled squeeze paddles 146 that allows the user to apply force or pressure to urge the paddles 146 together, enabling a quick expansion of the diameter of the tubular main body 142 and consequently of the opening of the scope accessory 10 for placement over the scope. In a resting position, however, the delivery assistance tool 140 does not stretch out or expand the scope accessory 10, as shown in FIG. 3B. As shown, the delivery assistance tool 140 may be used along with the insertion tool 60 described above. The delivery assistance tool 140 may be formed by wireform and overmolded with respect to the scope accessory 10, or it may be a separate plastic part that is inserted and packaged together with the scope accessory 10. A holder tab 156 may be provide with the tool 140 for ease of handling. The tool 40 may be formed of an elastomeric material to facilitate expansion.

FIGS. 4A to 4D illustrate another exemplary embodiment of a delivery assistance tool 240 that may be used along with insertion tool 60 of the delivery system 100. As shown, the delivery assistance tool 240 may be provided with a tubular main body 242 extending into a flared insertion collar 244 having a trumpet-like shape that may be broken off the scope after the scope accessory 10 is in place. The tubular main body 242 may include a slit 246 or cutout, slot or other design that allow the tubular main body 242 to expand and contract in diameter. The insertion collar 244 may be formed of rigid or semi-rigid material to hold the opening of the scope accessory 10 during insertion, stabilizing it from wrinkling or bunching. In addition to its flared shape, the collar 244 may include a cutaway portion 252, such as a V cut, to create a viewing window and give the user a view through the insertion collar 244 as the user aims the working channel extension shaft 66 of the insertion tool 60 through the accessory 10. The ramped shape of the insertion collar 48 guides the device or accessory 10 into and over the scope during use. Furthermore, the fluted shape of the collar 244 creates a flange ring grip to easily pull and separate the insertion collar 244 from the accessory 10 once the delivery process is completed.

Figure 4A:
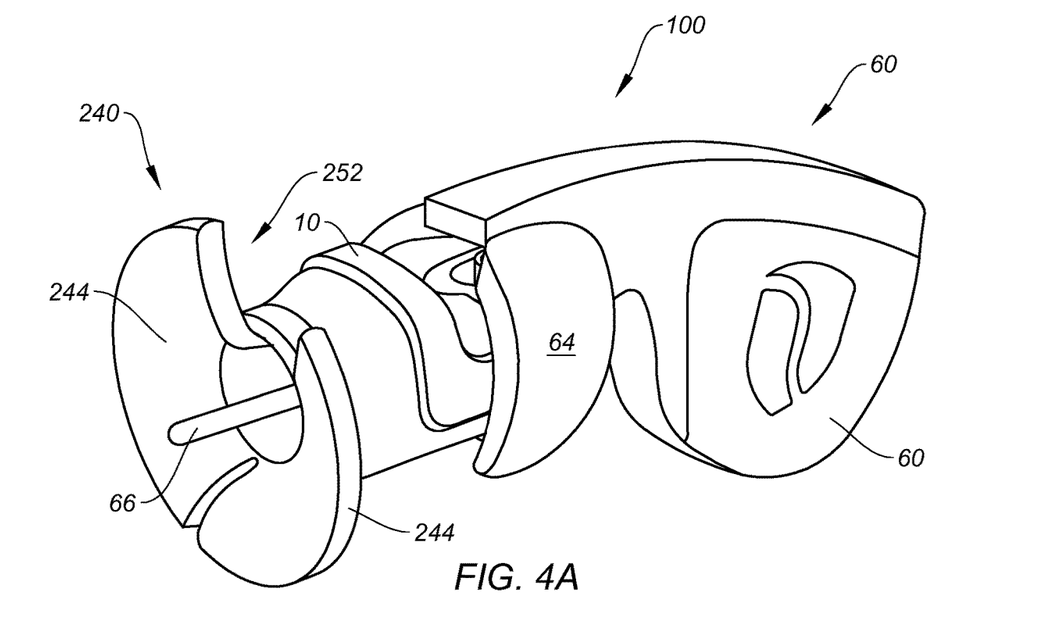
FIG. 4A shows a perspective view of a delivery assistance tool and delivery system in use with a scope accessory, in accordance with still another exemplary embodiment of the present disclosure.
Figure 4B:
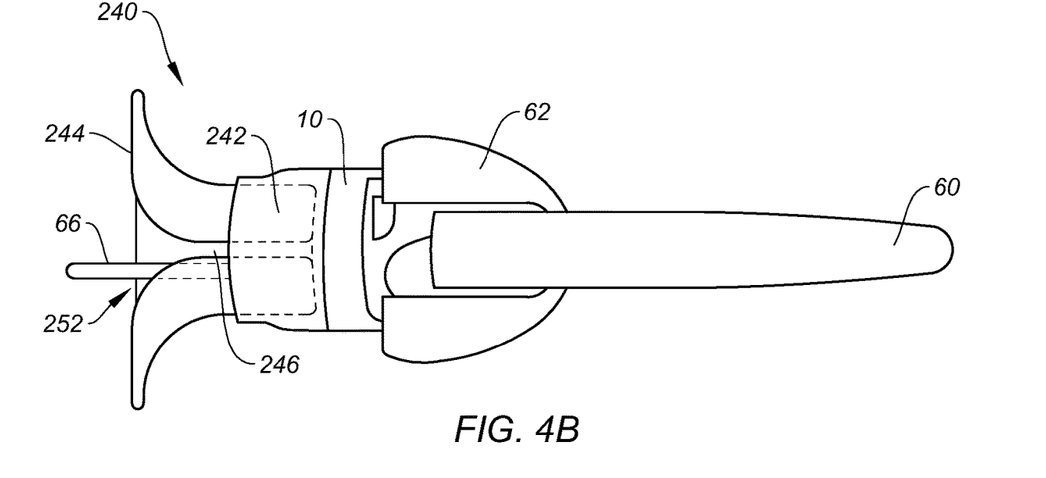
FIG. 4B illustrates a side view of the delivery system of FIG. 4A.
Figure 4C:
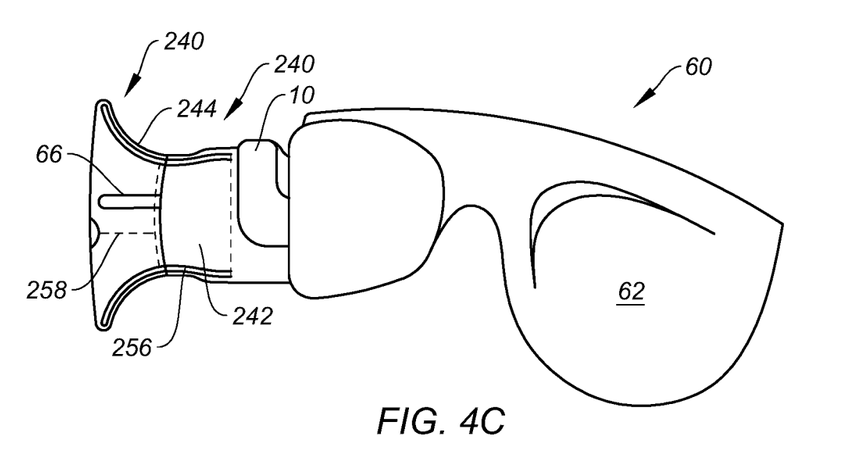
FIG. 4C illustrates a partial cutaway view of the system of FIG. 4B.
Figure 4D:
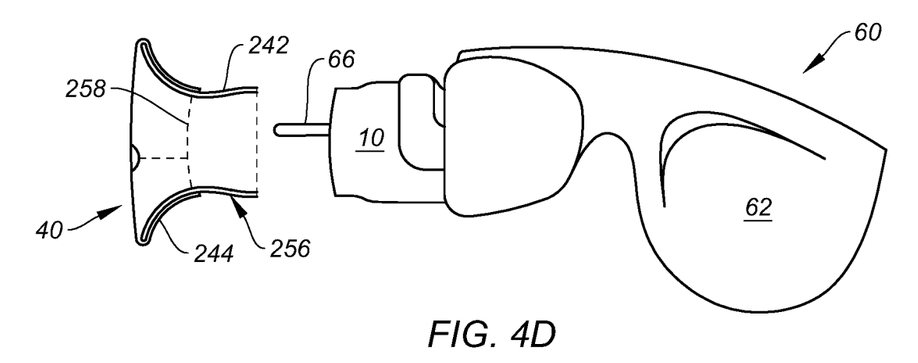
FIG. 4D illustrates an exploded view of the system of FIG. 4C.

As FIGS. 4C and 4D show, the flared collar 244 may be attached to the main tubular body 242 that is inserted into the accessory 10 by a glue bond that allows the flared collar 244 to tear away from the accessory 10 once delivery is complete. In an alternative embodiment, the flared collar 244 may include a tear away portion such as a scored or hatch marked area 248 that allows quick breaking away of the flared collar 244 from the scope accessory 10. The main tubular body 242 of the delivery assistance tool 240 may include surface features such as hard inner ribs 256 that support and stabilize the scope accessory 10 during this delivery process.

Figure 5A:
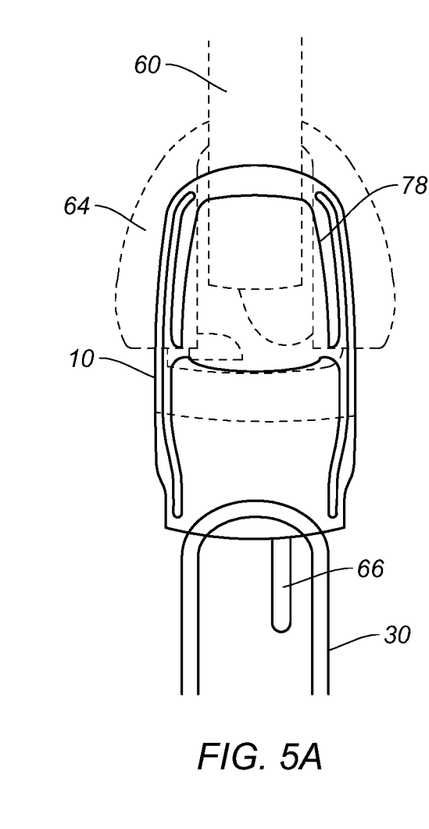
FIGS. 5A to 5C illustrate a method of delivering a scope accessory onto a scope, in accordance with yet another exemplary embodiment of the present disclosure.
Figure 5B:
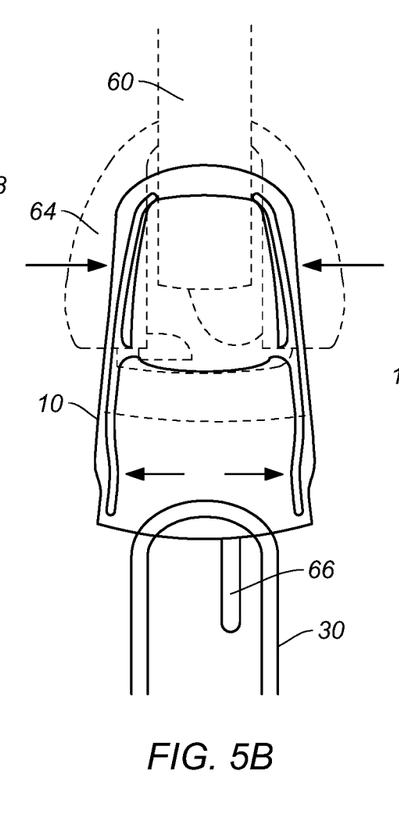
Figure 5C:
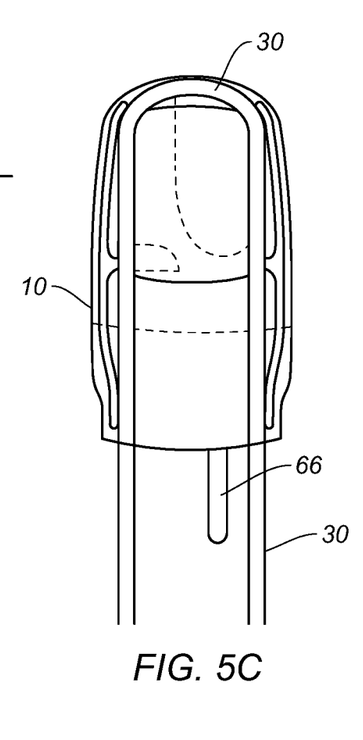

FIGS. 5A to 5C illustrate an exemplary method of applying the delivery system 100 to deliver a scope accessory 10 of the type having an elastomeric skirt onto a scope 30, in which FIGS. 5A and 5B shows the scope accessory 10 attached to the delivery tool 60 in a resting state (i.e., unexpanded). In some embodiments, a hard plastic co-molded component 78 may be provided that cooperates with the elastomeric portion of the scope accessory 10 such that, upon squeezing the nose of the scope accessory 10 in the direction of the arrows, the molded structure 78 which may be part of the optical window component opens up, as shown in FIG. 5B, thereby also expanding the elastomer of the scope accessory 10 and allowing it to more easily fit onto the scope 30, as shown in FIG. 5B. Releasing the force on the nose puts the scope accessory back in a resting state, as shown in 5C.

Figure 6A:
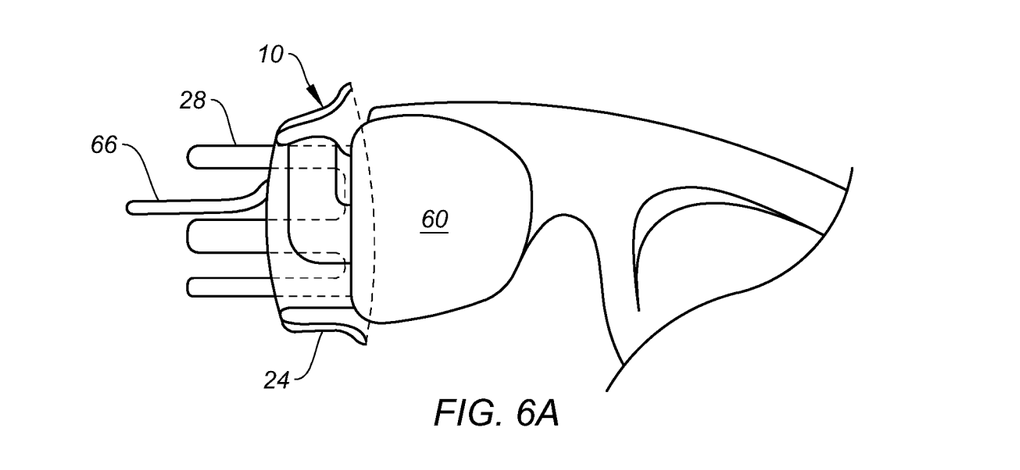
FIGS. 6A and 6B illustrate partial cutaway views of still another exemplary embodiment of the present disclosure in which the scope accessory of FIG. 1 may include internal ribs, in use with the delivery system of FIG. 1.
Figure 6B:
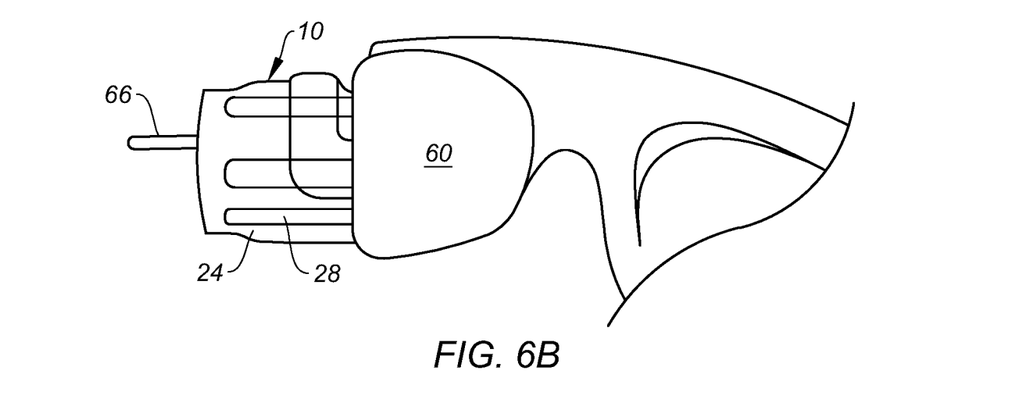

As shown in FIGS. 6A and 6B, hard plastic prongs 28 may be provide as part of the scope accessory 10. For instance, the scope accessory 10 may be provided with its elastomeric skirt 24 rolled back over itself to expose the prongs 28, which serve to help splint the elastomeric skirt 24 and keep it from bunching, while also providing a glide surface to facilitate insertion over the scope. When the elastomeric skirt 24 is rolled back over, the scope accessory 10 is properly sealed against the scope, as shown in FIG. 6B.

Figure 7A:
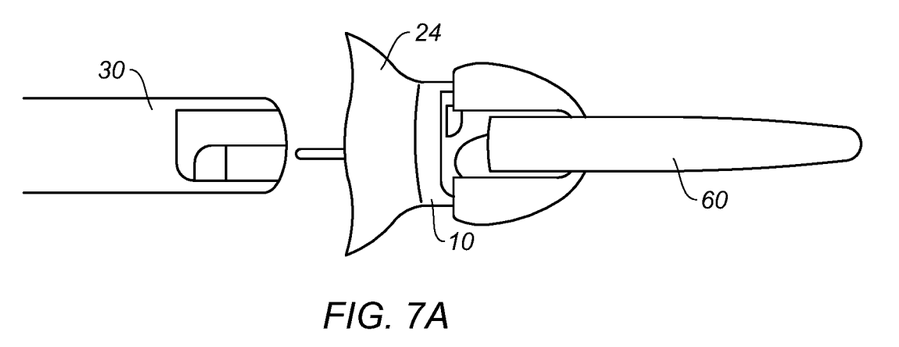
FIGS. 7A and 7B illustrate a method of inserting the scope accessory of FIGS. 6A and 6B before and after the application of heat.
Figure 7B:
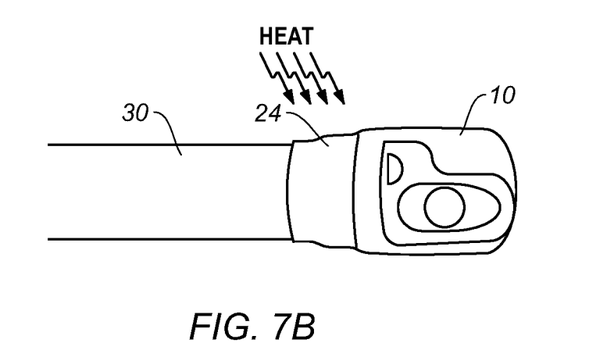

The elastomeric skirt 24 of the scope accessory 10 may be further secured onto the scope 30 after delivery by the application of heat, as illustrated in FIGS. 7A and 7B. The application of low heat to an elastomeric skirt formed of a heat-shrinking material, such as for example, fluorinated ethylene propylene (FEP), polytetrafluoroethylene (PTFE), polyester (PET), polyvinyl chloride (PVC), polyolefin, or any other suitable polymeric material, can cause the skirt 24 portion of the scope accessory to shrink around the scope 30, forming a tight seal.

As understood, the delivery system of the present disclosure provides a delivery assistance technology that improves the delivery of one or more medical devices or components over, onto, into, or against another medical device or component. The delivery assistance technology has the ability to modify the shape of one of the devices or components as it is delivered on to the other device or component, and to create a variety of capabilities, including through the delivery of force, the expansion or modification of geometries, and the addition of different coefficients of friction and other needed material properties to enable effective delivery of one component over, onto, into, or against another component.

The application of heat has been illustrated and describe with respect to FIGS. 7A and 7B. However, it is understood that other applications may include the use of energy, temperature, surface modifications, and additives, in order to facilitate the smooth delivery of the component or device. For example, temperature sensitive materials like a Nitinol or other electrically responsive or shape-memory alloy or material may be utilized along with the application of heat (such as from body heat when inside the body) to adjust and alter shapes from an open configuration to a closed configuration. In addition, additives may be utilized to reduce the coefficient of friction and facilitate smooth sliding off motion during delivery, such as polymer oils, silicone oils or with the addition of coatings of a polymer like PTFE. In still other embodiments, surface modifications may be provided to facilitate delivery. A highly polished, mirror-like finish may be utilized for a smooth, gliding surface during delivery, while in an alternative design, a roughened surface may be utilized to decrease the grip or adherence between the component and the delivery system to enable faster release from the delivery tools 40, 60 and onto the scope 30.

Figure 8:
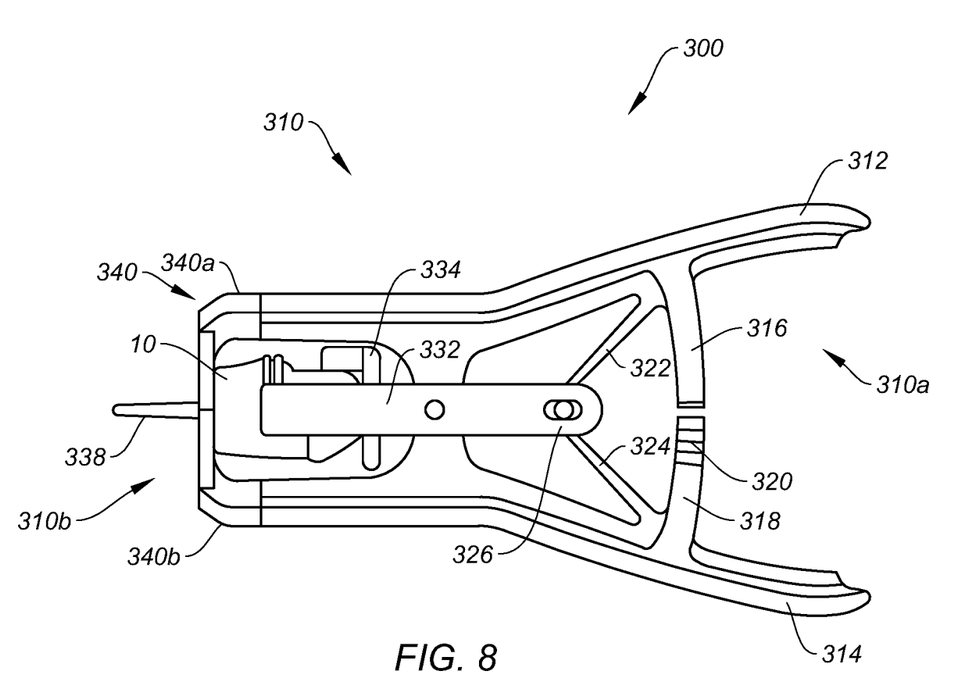
FIG. 8 illustrates a top-down view of an exemplary embodiment of a delivery system of the present disclosure, attached to a scope accessory.

FIG. 8 illustrates another exemplary embodiment of a delivery system 300 of the present disclosure. This delivery system 300 includes an insertion instrument 310 and an end cap or spacer 340. The insertion instrument 310 may be provided with a pre-mounted scope accessory 10 in the configuration shown in FIG. 8. The insertion instrument 310 has a handle portion or end 310a, and a working or delivery end 310b.

As shown, the insertion instrument 310 may generally have the structure and functionality of delivery pliers, and include a first or upper arm 312 and a second or lower arm 314. These arms 312, 314 may be connected to one another at a hinged or pivotal connection 326 through secondary arm extensions 322, 324, respectively. The insertion instrument 310 may also include an attached main bracket 332 which is stationary relative to the pivotable or movable arms 312, 314. A back plate or wall 334 can be connected to this main bracket 332 for supporting the scope accessory 10 within the delivery system. The back plate 334 may be connected to a stabilizing extension shaft 338, similar to the extension shaft 66 of insertion tool 60, which may be inserted through a working channel opening of the scope accessory 10. The stabilizing extension shaft 338 may have a blunt tip, for example, to avoid damage to the scope accessory 10 or scope 30, in use. In its pre-assembled configuration, the scope accessory 10 is secured against the back plate 334 of the main bracket, as illustrated.

As further shown, each of the upper and lower arms 312, 314 also includes stabilizing or side bars 316, 318, respectively. The stabilizing side bars 316, 318 are configured to work with one another. As shown, each of the stabilizing side bars 316, 318 may have a ratcheting surface or feature 320 such as teeth, ridges, or other surface protrusions, that allows the stabilizing side bars 316, 318 to lock together and prevent movement of the arms 312, 314 relative to one another.

An end cap or spacer 340 is provided for use with the insertion instrument 310. This spacer 340 comprises a two-piece design and includes spacer components 340a, 340b. The spacer 340 can be placed at the working end 310b of the insertion instrument 310, and may be configured to attach to the scope accessory 10. In one embodiment, the spacer 340 is configured so that it expands the opening of the scope accessory 10 for placement over the distal end of the scope 30. Collectively, these spacer elements 340a, 340b form an additional delivery assistance tool for delivering the scope accessory 10 at the working or delivery end 310b of the insertion instrument 310 to the scope 30.

FIGS. 9A to 9H illustrate an exemplary method of using the insertion instrument 310 of the present disclosure to insert a scope accessory 10 onto a scope 30. With the scope 30 securely held in one hand, the scope 30 being properly aligned and positioned to receive the scope accessory 10, the user may grip the handle portion 310a of the insertion instrument 310 with the other hand. The user may squeeze the upper and lower arms 312, 314 in the direction of the arrows shown in FIG. 9A, to release or unlock the arms with respect to one another.

Figure 9A:
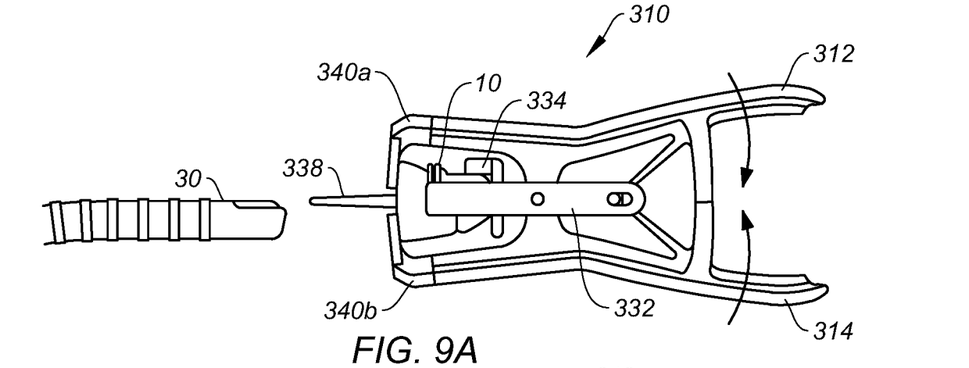
FIGS. 9A to 9H illustrates a method of using the delivery system of FIG. 8 to insert the scope accessory onto a scope.
Figure 9B:
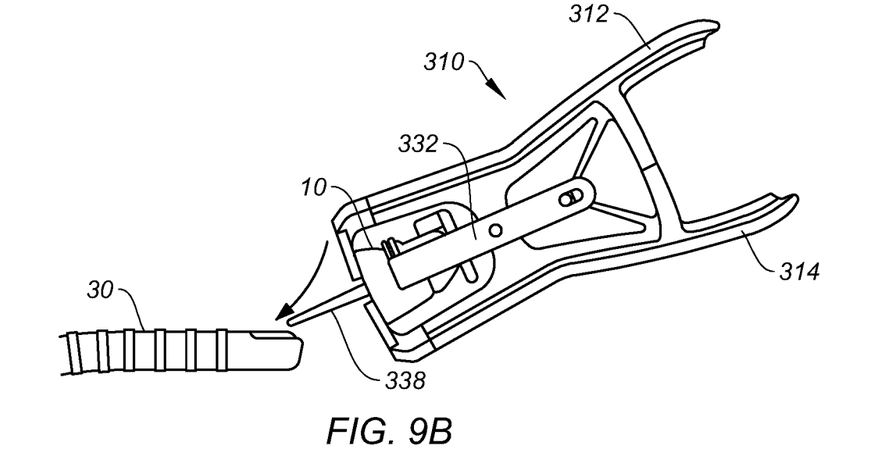

The extension shaft 338 of the insertion instrument 310 may serve as an alignment guide in the next step shown in FIG. 9B, allowing the user to guide the insertion instrument 310 with the pre-assembled scope accessory 10 towards the scope 30 and into its working channel. Once the extension shaft 338 is introduced through the working channel of the scope, the insertion instrument 310 can be advanced. In one embodiment, the advancement is done at an angle of about 45 degrees. However, it is understood that the insertion instrument 310 may be advanced at any angle, including in the range of about 30 to about 60 degrees, depending on the configuration of the scope 30 and using the best judgment of the user. Additionally, the angle at which the insertion instrument 310 is advanced will change depending on the stage of the assembly process. In other words, the angle of approach will change as the scope accessory 10 is advanced further onto the scope 30.

Figure 9C:
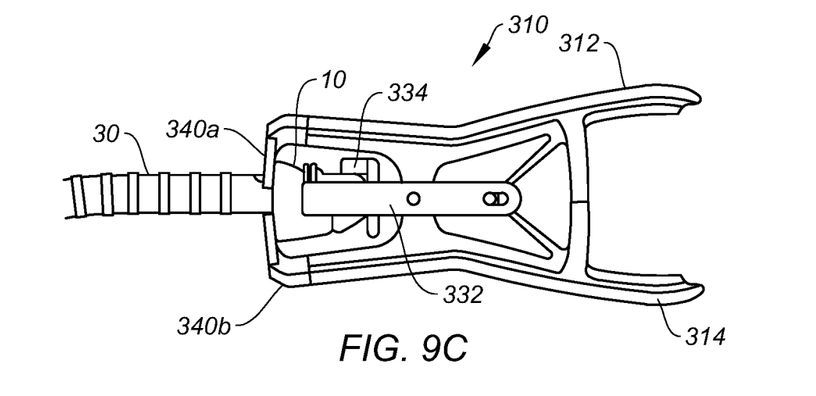
Figure 9D:
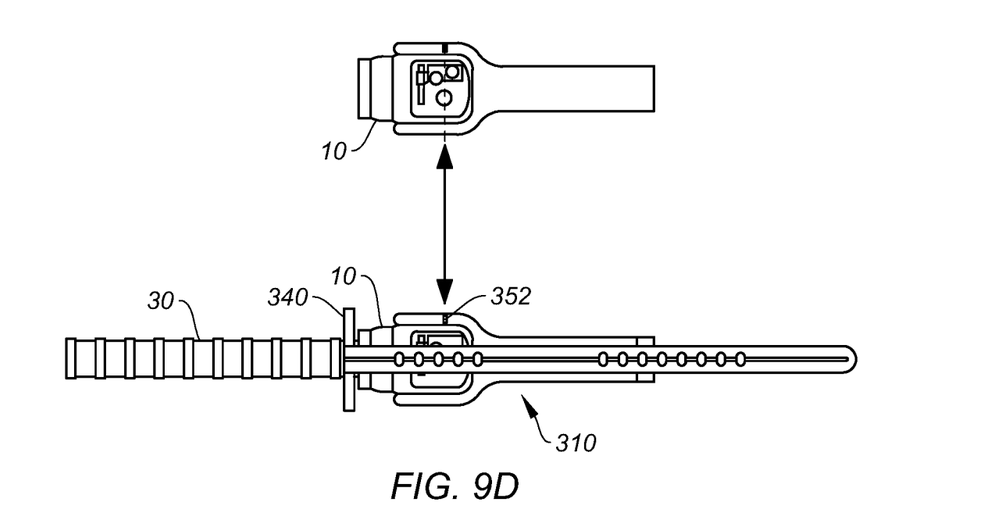

The insertion instrument 310 may be advanced or urged forward until the receiving end of the scope accessory 10 is on the distal end of the scope, as shown in FIG. 9C. Indicia 352 on the insertion instrument 310 serves as a convenient visual alignment guide to enable the user to determine the appropriate position of the scope accessory 10 during assembly, as shown in FIG. 9D. The indicia 352 may be checked to ensure that the optical area of the scope accessory 10 is aligned with the optical area of the scope 30, for example, thus ensuring a proper aligned fit. The insertion instrument 310 should not be advanced any further at this point. As further shown in FIG. 9C, the delivery end 310b of the insertion instrument 310 has expanded, while the handle end 310a remains unexpanded.

Figure 9E:
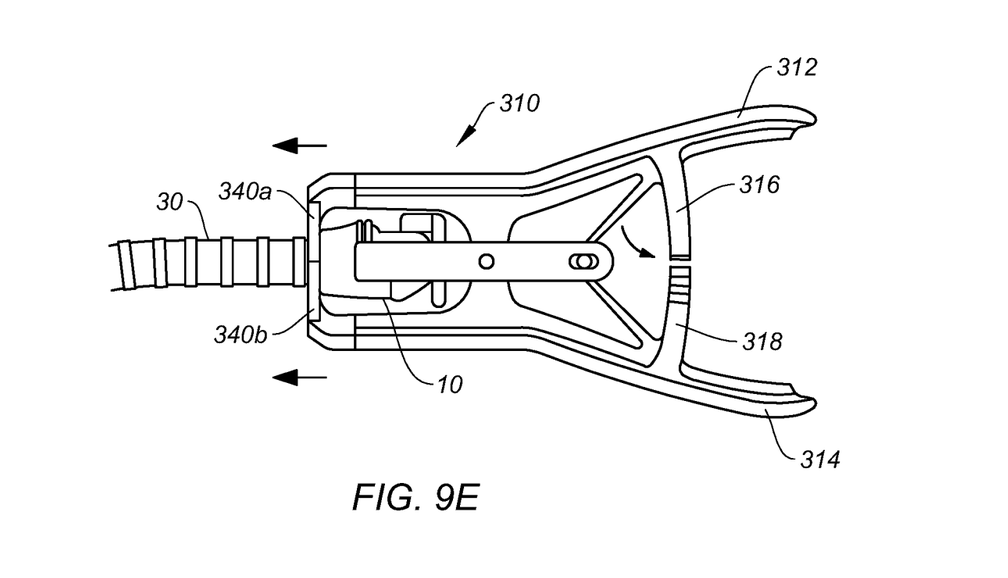
Figure 9F:
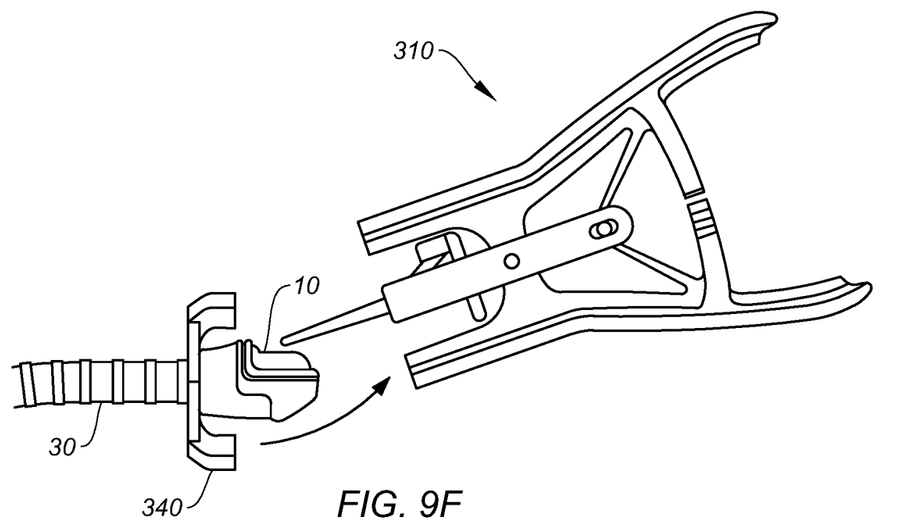

Turning now to FIG. 9E, after proper positioning and alignment of the scope accessory 10 on the scope 30 has been confirmed, the upper and lower arms 312, 314 of the insertion instrument 310 may be unlocked. This can be accomplished by pushing against the stabilizing side bars 316, 318 to unseat them from one another. This unlocking of the arms 312, 314 allows the insertion instrument 310 to return to a resting or unexpanded state, as shown in FIG. 9E. Grasping the spacer 340 as a single unit, the user may then pull this spacer 340 away from the delivery end 310b of the insertion instrument 310. Removal of the spacer 340 then allows the insertion instrument 310 to be withdrawn, as shown in FIG. 9F along the angled direction of the arrow, to avoid any damage to the scope in the process.

Figure 9G:
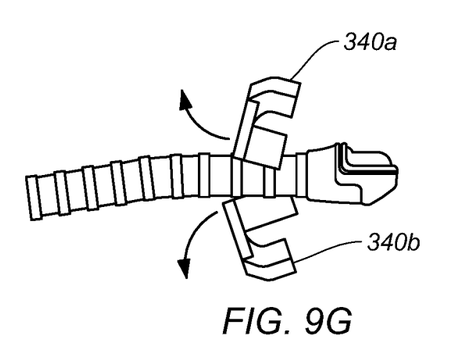
Figure 9H:
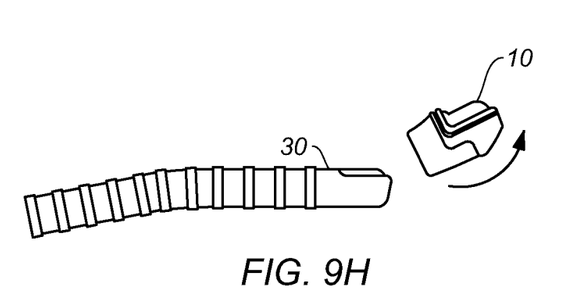

Upon the completion of the assembly process, the spacer 340 remaining on the scope 30 may be broken apart and each of the components 340a, 340b may be removed, as shown in FIG. 9G. If the scope accessory 10 is misaligned or improperly positioned on the scope 30, the user may manually remove the scope accessory 10 by pulling it away and upward off the scope 30, as shown in FIG. 9H, and start the process again.

It is contemplated that the systems 100, 300, including the tools 40, 60, 140, 240, may be formed of any material, including but not limited to, elastic, plastic or deformable or malleable materials, whether metal or polymer, or derivatives or combinations thereof.

It is of course understood that the delivery systems 100, 300 may be sterilized using any acceptable method or may be non-sterile. For example, the delivery systems 100, 300 may be provided as a disposable or single-use system or instrument.

Moreover, while the present illustrations show embodiments in which the scope accessory 10 is expanded or stretched in order to fit over or onto the scope 30, it is also contemplated that a delivery system may be provided which is configured to contract or compress the scope accessory 10 in order to have it fit inside the scope 30, and then allow the scope accessory to expand into its natural resting state and thereby form a tight seal within the scope 30.

Other embodiments will be apparent to those skilled in the art from consideration of the specification and practice of the embodiment disclosed herein. It is intended that the specification and examples be considered as exemplary only.

What is claimed is:

1. A device delivery system comprising:
   an accessory device comprising a main body, a proximal end configured for attaching to a distal end of an endoscope and a working channel configured for receiving an instrument;
   an insertion instrument having a pair of pivotable arms, the arms extending from a device delivery portion of the insertion instrument at a first end, into a handle portion at an opposed, second end, and connected together at a pivotable connection, a bracket connected to a back plate for placement of the accessory device, and an extension shaft extending from the back plate and configured for placement through the working channel of the accessory device; and
   a removable spacer for enclosing the device delivery portion of the insertion instrument.

2. The delivery system of claim 1, wherein the pivotable arms further include stabilizing side bars configured to allow the pivotable arms to lock together.

3. The delivery system of claim 2, wherein the stabilizing side bars include a ratcheting surface.

4. The delivery system of claim 1, wherein the bracket is stationary with respect to the pivotable arms.

5. The delivery system of claim 1, wherein the extension shaft is configured as an alignment guide for delivery of the device.

6. The delivery system of claim 1, wherein the removable spacer comprises two detachable components.

7. The delivery system of claim 1, wherein the removable spacer is configured to expand an opening of the device to be delivered.

8. The delivery system of claim 1, wherein the pivotable arms are movable away from one another at the first end upon movement of the pivotable arms at the second end.

9. The delivery system of claim 1, further including indicia for use as an alignment guide.

10. The delivery system of claim 9, wherein the indicia represents positioning of an optical area of an endoscopic device to be delivered and an optical area of an endoscope on which the device is to be attached.

* * * * *